United States Patent [19]

Wagner et al.

[11] 4,414,004
[45] Nov. 8, 1983

[54] REMOVAL OF CONDENSABLE ALIPHATIC HYDROCARBONS AND ACIDIC GASES FROM NATURAL GAS

[75] Inventors: Eckhart Wagner, Ludwigshafen; Ulrich Wagner, Limburgerhof; Klaus Volkamer, Frankenthal; Wolfgang Vodrazka, Freinsheim, all of Fed. Rep. of Germany

[73] Assignee: BASF Aktiengesellschaft, Fed. Rep. of Germany

[21] Appl. No.: 356,721

[22] Filed: Mar. 10, 1982

[51] Int. Cl.³ .............................................. B01D 53/14
[52] U.S. Cl. .......................................... 55/48; 55/54; 55/73
[58] Field of Search ..................... 55/30, 31, 48, 54, 73

[56] References Cited

U.S. PATENT DOCUMENTS

| | | | |
|---|---|---|---|
| 2,139,375 | 12/1938 | Millar et al. | 55/73 |
| 2,781,863 | 2/1957 | Bloch et al. | 55/73 X |
| 3,594,985 | 7/1971 | Ameen et al. | 55/73 X |
| 3,739,548 | 6/1973 | Hegwer | 55/48 X |
| 3,770,622 | 11/1973 | Freireich et al. | 55/73 X |
| 3,824,766 | 7/1974 | Valentine et al. | 55/48 |
| 3,855,337 | 12/1974 | Foral, Jr. et al. | 55/31 |
| 4,106,917 | 8/1978 | Fields et al. | 55/31 |
| 4,302,220 | 11/1981 | Volkamer et al. | 55/48 X |
| 4,330,305 | 5/1982 | Kuessner et al. | 55/73 X |

OTHER PUBLICATIONS

Oil and Gas Journal, Jan. 12, 1980, pp. 66-70.

*Primary Examiner*—Robert H. Spitzer
*Attorney, Agent, or Firm*—Keil & Witherspoon

[57] ABSTRACT

A process for removing condensable aliphatic hydrocarbons and acidic gases such as $H_2S$, $CO_2$ and COS from natural gas containing these, wherein the natural gas is initially treated with polyethylene glycol dialkyl ethers, as the solvent, in a first absorption stage to effect absorption of the condensable aliphatic hydrocarbons; the natural gas drawn off from the first absorption stage is then treated with polyethylene glycol dialkyl ethers, as the solvent, under superatmospheric pressure in a second absorption stage, the acidic gases being completely or partly absorbed; the solvent charged with the condensable aliphatic hydrocarbons which is obtained from the first absorption stage is treated with water in an extraction stage, to form a hydrocarbon phase containing the condensable aliphatic hydrocarbons and an aqueous dialkyl ether phase, and the hydrocarbon phase is separated from the aqueous dialkyl ether phase. The solvent charged with acid gases which is obtained from the second absorption stage is regenerated by expansion and/or stripping in a regeneration stage and the regenerated solvent is recycled to the absorption.

9 Claims, 1 Drawing Figure

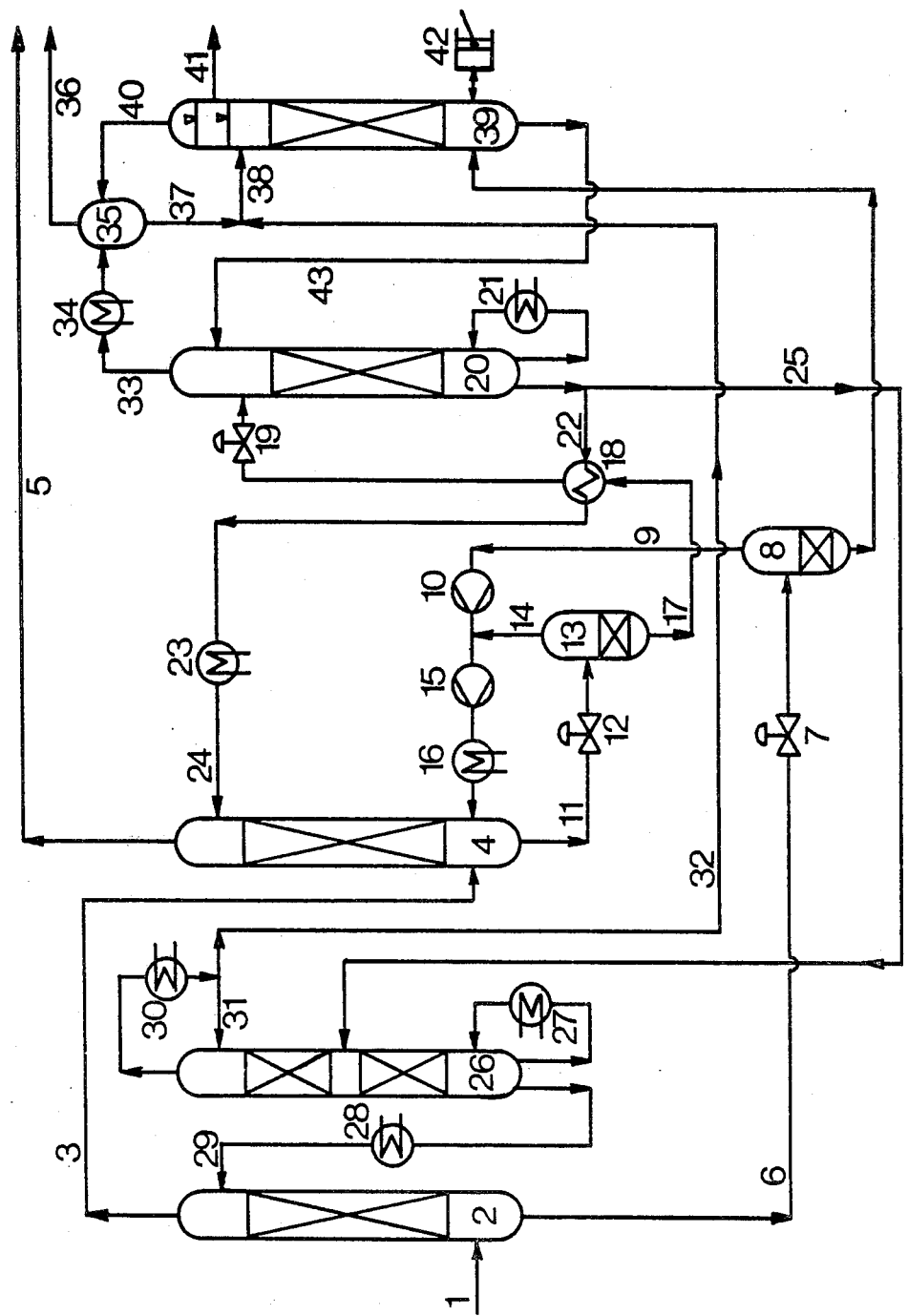

REMOVAL OF CONDENSABLE ALIPHATIC HYDROCARBONS AND ACIDIC GASES FROM NATURAL GAS

The present invention relates to a process for removing condensable aliphatic hydrocarbons and acidic gases such as $H_2S$, $CO_2$ and/or COS from natural gas containing these, by treating the natural gas with polyethylene glycol dialkyl ethers.

Oil and Gas Journal, Jan. 21, 1980, pages 66 to 70, for example, discloses the removal of acidic components from natural gas using polyethylene glycol dialkyl ethers, which act as physical solvents. This procedure is particularly suitable for removing acidic components, especially for selectively removing sulfur-containing components, from dry natural gas, ie. natural gas in which the hydrocarbon component is substantially methane. In contrast, the conventional process is unsuitable for removing acidic components from wet natural gas, ie. natural gas which, besides methane, also contains higher aliphatic hydrocarbons.

Instead, chemical solvents, for example an aqueous solution of an alkanolamine such as diethanolamine, have hitherto been used for working up a wet natural gas in industrial natural gas scrubbers. Treatment of the wet natural gas with an aqueous alkanolamine solution removed the acidic components, whilst the higher aliphatic hydrocarbons passed through the natural gas wash and were then isolated by condensation. However, the condensation stage had to be preceded by an expensive drying stage in order again to remove the water vapor taken up by the natural gas during treatment with the aqueous alkanolamine solution. A further disadvantage of chemical solvents is that they generally have only a low selectivity towards $CO_2$ in respect of removal of the sulfur-containing acidic components.

It is an object of the present invention to provide a process for removing condensable aliphatic hydrocarbons and acidic gases such as $H_2S$, $CO_2$ and COS from natural gas containing these, which enables the use of chemical solvents and the resulting disadvantages in working up natural gas to be dispensed with.

We have found that this object is achieved and other advantages are gained by a process for removing condensable aliphatic hydrocarbons and acidic gases such as $H_2S$, $CO_2$ and COS from natural gas containing these condensable aliphatic hydrocarbons and acidic gases wherein (a) the natural gas is initially treated with polyethylene glycol dialkyl ethers, as the solvent, in a first absorption stage to effect absorption of the condensable aliphatic hydrocarbons, (b) the natural gas drawn off from the first absorption stage is then treated with polyethylene glycol dialkyl ethers, as the solvent, under superatmospheric pressure in a second absorption stage, the acidic gases completely or partly being absorbed, (c) the solvent charged with condensable aliphatic hydrocarbons which is obtained from the first absorption stage is treated with water in an extraction stage to form a hydrocarbon phase containing the condensable aliphatic hydrocarbons and an aqueous dialkyl ether phase, and the hydrocarbon phase is separated from the aqueous dialkyl ether phase, (d) the solvent charged with acidic gases which is obtained from the second absorption stage is regenerated by expansion and/or stripping in a regeneration stage and (e) the regenerated solvent is recycled to the absorption.

In addition to the removal of the sulfur compounds contained in wet natural gas, all or some of the higher aliphatic hydrocarbons contained therein can also be removed in a simple manner in the new process, so that the natural gas obtained after working up can be fed into the gas distribution network without troublesome liquefaction and separating out of the higher aliphatic hydrocarbons occuring at low temperatures. The higher aliphatic hydrocarbons separated off are important starting materials for petrochemical processes, for example for the preparation of ethylene.

In addition to the main component, methane, and the acidic gases such as $H_2S$, $CO_2$ and/or COS, the natural gas to be used according to the invention generally contains varying amounts of hydrocarbons of 2 to 15, preferably of 2 to 10, carbon atoms, from the aliphatic homologous series. As a rule the concentration of these aliphatic hydrocarbons in the natural gas is from 0.1 to 10 mole %.

The amount of hydrogen sulfide to be removed from the gas can also vary within wide limits. The gas to be used generally has a hydrogen sulfide content of not less than 5 ppm by volume, preferably not less than 10 ppm by volume, especially not less than 100 ppm by volume, and as a rule not more than 50% by volume, preferably not more than 40% by volume and especially not more than 30% by volume. The natural gas to be employed may contain COS as another sulfur-containing acidic component, for example in an amount of from 3 ppm by volume to 2% by volume.

In addition to hydrogen sulfide, the gas to be employed frequently contains carbon dioxide as another acidic gas, for example in an amount of from 0.01 to 60% by volume, preferably from 0.1 to 45% by volume and especially from 0.1 to 30% by volume.

In general, suitable polyethylene glycol dialkyl ethers are those of the general formula

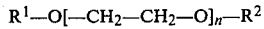

$$R^1-O[-CH_2-CH_2-O]_n-R^2$$

where $R^1$ and $R^2$ can be identical or different and each is branched or straight-chain $C_1$–$C_5$-alkyl, preferably $C_1$–$C_4$-alkyl, and n indicates the number of ethylene glycol groups and is an integer from 2 to 9, preferably from 3 to 8. Dialkyl ethers where $R^1$ and $R^2$ are hydrocarbon radicals are advantageously used. Examples of suitable radicals $R^1$ and $R^2$ are methyl, ethyl, n-propyl, isopropyl, n-butyl, isobutyl and tert.-butyl, and the amyl radicals, such as tert.-amyl.

Examples of suitable polyethylene glycol dialkyl ethers are the dimethyl, methyl ethyl, methyl n-propyl, methyl isopropyl, methyl n-butyl, methyl isobutyl, methyl tert.-butyl, methyl tert.-amyl, diethyl, ethyl n-propyl, ethyl isopropyl, ethyl n-butyl, ethyl isobutyl, ethyl tert.-butyl, ethyl tert.-amyl, di-n-propyl, di-isopropyl, n-propyl isopropyl, n-propyl n-butyl, n-propyl isobutyl, n-propyl tert.-butyl, n-propyl tert.-amyl, isopropyl n-butyl, isopropyl isobutyl, isopropyl tert.-butyl and isopropyl tert.-amyl ethers. Dimethyl and methyl isopropyl ethers are preferably used. Polyethylene glycol dialkyl ethers with the same number n of ethylene glycol groups can be used. In practice, however, mixtures of polyethylene glycol dialkyl ethers having in general from 2 to 8 ethylene glycol groups are as a rule used.

According to the invention, the natural gas to be worked up is first treated with polyethylene glycol dialkyl ethers, as the solvent, in a first absorption stage for absorption of the condensable aliphatic hydrocarbons. Advantageously, the solvent in the first absorption stage contains from 0.5 to 8% by weight, preferably from 0.5 to 5% by weight, of water. The first absorption stage can be operated under atmospheric pressure. Advantageously, however, superatmospheric pressure, generally of from 5 to 150 bar, preferably from 10 to 130 bar and especially from 20 to 120 bar, is maintained in the first absorption stage. As a rule, the first absorption zone is operated at from $-20°$ to $+60°$ C., preferably from $-20°$ to $+40°$ C., and advantageously as an absorption column, generally as a packed column or tray column, the solvent advantageously being fed into the top half, preferably into the top one-third, and generally being led in countercurrent to the gas to be treated.

The natural gas drawn off from the first absorption stage is then again treated with polyethylene glycol dialkyl ethers, as the solvent, under superatmospheric pressure in a second absorption stage for absorption of the acidic components such as $H_2S$, $CO_2$ and/or COS. Advantageously, the solvent fed into the second absorption stage contains more water than that fed into the first absorption stage, generally from 1.5 to 14% by weight, preferably from 2 to 10% by weight. Advantageously, the same polyethylene glycol dialkyl ether or the same dialkyl ether mixture is used in the second absorption stage as in the first.

A superatmospheric pressure of from 5 to 150 bar, preferably from 10 to 130 bar, especially from 20 to 120 bar, is in general maintained in the second absorption stage. Advantageously, the first and second absorption stages are operated under the same pressure.

The second absorption stage is as a rule operated at from $-20°$ to $+60°$ C., preferably from $-20°$ to $+40°$ C., and advantageously as an absorption column, generally as a packed column or tray column, the solvent advantageously being fed into the top half, preferably into the top one-third, and generally being led in countercurrent to the gas to be treated.

If the natural gas to be treated in the second absorption stage contains hydrogen sulfide and carbon dioxide as acidic gases, these two gases can be removed together in the second absorption stage. However, in an advantageous embodiment of the process according to the invention, if the gas contains carbon dioxide, the hydrogen sulfide is removed selectively in the second absorption zone. The amount of solvent used in the second absorption stage is generally several times the amount required for the first absorption stage, for example from 2 to 100 times, preferably from 5 to 50 times, the amount.

The solvent charged with condensable aliphatic hydrocarbons which is obtained from the first absorption stage is treated with water in an extraction stage. Advantageously, the solvent charged with hydrocarbons is mixed with water to form a hydrocarbon phase containing the condensable aliphatic hydrocarbons and an aqueous dialkyl ether phase. The aliphatic hydrocarbons can be obtained in a pure, liquid form by separating off the hydrocarbon phase. In general, the solvent charged with the hydrocarbons is treated with such an amount of water that the aqueous dialkyl ether phase which forms contains from 16 to 90% by weight, preferably from 20 to 80% by weight, of water. The extraction stage is advantageously operated by leading the solvent charged with hydrocarbons in countercurrent to the water introduced into the extraction stage. Suitable extraction apparatuses are, for example, those of the mixer/settler type, countercurrent columns with rotating internal fitments (eg. a rotating disc contactor) or pulsating packed columns. The extraction stage can be operated under atmospheric pressure or under superatmospheric pressure of, for example, from 1 to 30 bar.

The solvent charged with acidic gases which is obtained from the second absorption stage is regenerated in a regeneration stage, the acidic gases being expelled. Regeneration can be effected by expansion of the solvent charged with acidic gases in an expansion zone to a pressure below the absorption pressure, or by stripping off the acidic gases in a desorption zone, advantageously using steam as the stripping agent. In a preferred embodiment, the solvent charged with the acidic gases first undergoes flash evaporation in an expansion zone. The gas mixture obtained from flash evaporation is advantageously recycled to the second absorption zone, by which means losses of partly dissolved valuable products such as methane and ethane are kept to a minimum. The solvent obtained from the expansion zone is then stripped with steam in a downstream desorption zone, the dissolved acidic gases being virtually completely stripped from the solvent. If the second absorption stage is operated with selective removal of $H_2S$, highly concentrated $H_2S$ gas can be produced during stripping by means of steam in the desorption stage, and this can be worked up to elementary sulfur, for example in a Claus unit.

In a particular embodiment of the process, the desorption zone operated with steam stripping, and the extraction stage, can be linked by a closed water/solvent circuit. This is advantageously effected by a procedure in which the water which, when the solvent charged with acidic gases is stripped with steam in the desorption zone, is obtained as condensate, advantageously by cooling the acidic gases which have been stripped off and contain relatively large quantities of steam in a condensation zone downstream of the desorption zone, is used for treating the solvent charged with condensable aliphatic hydrocarbons in the extraction stage. At the same time, to complete the circuit, the aqueous dialkyl ether mixture obtained after phase separation in the extraction stage is recycled to the desorption zone, into the top of which the mixture is advantageously introduced as a liquid reflux.

The regenerated solvent removed at the bottom of the desorption zone is recycled to the absorption. It is passed to the second absorption stage, generally with the same water content with which it has been removed from the desorption zone. In contrast, the water content of the regenerated solvent which is introduced into the first absorption stage is in general advantageously reduced by distilling off the water beforehand.

The Example below illustrates further details of the invention. The course of the process is shown schematically in the FIGURE.

A gas containing hydrogen sulfide, carbon dioxide and aliphatic hydrocarbons and having the composition given in the Table is introduced under superatmospheric pressure into the bottom of absorption column 2 via line 1. At the same time, a quantity of solvent which consists of a mixture of polyethylene glycol dialkyl ethers and a residual amount of water and is cooled in a cooler 28 is introduced at the top of the absorption column via line 29. This solvent is passed in countercurrent to the gas and dissolves most of the usually liquid hydrocarbons and small amounts of the acidic components $H_2S$ and $CO_2$ out of the gas mixture to be treated. The gas is drawn off via line 3 at the top of the column 2 and is then introduced into the bottom of the absorption column 4. A cooled stream of solvent is likewise introduced into column 4, via line 24. In general, the amount flowing through line 24 is many times the amount flowing through line 29. At the top of the column 4, a pure gas which still has only a low content of higher hydrocarbons and the acidic components $H_2S$ and/or $CO_2$ is removed via line 5. The solvent stream 6 charged with higher hydrocarbons is expanded to atmospheric pressure in a flash evaporation tank 8 via valve 7. The usually gaseous components which have dissolved in the absorption column 2 are thereby desorbed, and are passed to the compressor 10 via line 9. The charged solvent from absorption column 4 is expanded in the flash evaporation tank 13 via line 11 and valve 12. In this tank, dissolved gas is desorbed, the amount depending on the expansion pressure. The expansion gas is mixed via line 14 with the previously compressed expansion gas from tank 8, compressed in compressor 15 to the absorption pressure in column 4, cooled in the cooler 16 and then recycled to the absorption column 4. The solvent removed at the bottom of the expansion tank 13 is passed via line 17 to the heat exchanger 18 and, after expansion in valve 19, to the top of the absorption column 20, in which the acidic components are stripped off by ascending steam and are released via line 33 after condensation of the steam in condenser 34 and deposition of the condensed water in tank 35 via line 36. The steam required for stripping off the acidic compounds is produced in boiler 21 by indirect contact of the regenerated solvent with a heating medium, and is passed upwards in desorption column 20 towards the solvent to be stripped. Most of the solvent removed from the bottom of column 20 is cooled in the heat exchangers 18 and 23 via line 22 and is introduced into the top of absorption column 4 via line 24. A smaller amount is passed via line 25 to a column 26, in which the water content is decreased by distillation. The solvent with a reduced water content is removed at the bottom of column 26 and, after cooling in heat exchanger 28, is passed to the top of absorber 2 via line 29. Part of the bottom product of column 26 is recycled to column 26 via boiler 27. The water vapor which leaves column 26 as the top product is liquefied in condenser 30; some of this water is introduced into the top of column 26 via line 31 as a liquid reflux, and some is mixed via line 32 with the condensed water coming via line 37 from tank 35. The combined streams of water are introduced into the top part of extaction column 39 via line 38. The mixture of polyethylene glycol dialkyl ethers and hydrocarbons introduced into the bottom part of column 39 mixes with the water, whereupon separation into an aqueous dialkyl ether phase on the one hand and a liquid hydrocarbon phase on the other hand takes place. The liquid hydrocarbons separate out at the top of the column and are there removed via line 41. The column is connected to tank 35 via the venting line 40. The aqueous stream of dialkyl ethers removed at the bottom of the column is introduced into the top of desorption column 20 via line 43. Thorough mixing of the aqueous and organic phases in the extraction column 39 is ensured with the aid of the pulsation pump 42.

TABLE

| Typical compostion of acidic natural gas containing higher hydrocarbons | |
|---|---|
| Component | Concentration (mole %) |
| $N_2$ | 3.2 |
| $CO_2$ | 4.3 |
| $H_2S$ | 1.0 |
| $CH_4$ | 84.9 |
| $C_2H_6$ | 5.3 |

TABLE-continued

| Typical composition of acidic natural gas containing higher hydrocarbons | |
|---|---|
| Component | Concentration (mole %) |
| $C_3H_8$ | 0.65 |
| i-$C_4H_{10}$ | 0.32 |
| n-$C_4H_{10}$ | 0.12 |
| $C_5H_{12}$ | 0.09 |
| $C_6H_{14}$ | 0.05 |
| $C_7H_{16}$ | 0.05 |
| $C_8+$ | 0.02 |

We claim:

1. A process for removing condensable aliphatic hydrocarbons and acidic gases such as $H_2S$, $CO_2$ and COS from natural gas containing these, which comprises:
   (a) initially treating the natural gas with polyethylene glycol dialkyl ethers, as the solvent, in a first absorption stage to effect absorption of the condensable aliphatic hydrocarbons,
   (b) then treating the natural gas drawn off from the first absorption stage with polyethylene glycol dialkyl ethers, as the solvent, under superatmospheric pressure in a second absorption stage, the acidic gases completely or partly being absorbed,
   (c) treating the solvent charged with condensable aliphatic hydrocarbons which is obtained from the first stage with water in an extraction stage to form a hydrocarbon phase containing the condensable aliphatic hydrocarbons and an aqueous dialkyl ether phase, and separating the hydrocarbon phase from the aqueous dialkyl ether phase,
   (d) regenerating the solvent charged with acidic gases which is obtained from the second absorption stage by expansion and/or stripping in a regeneration stage and
   (e) recycling the regenerated solvent to the absorption.

2. A process as claimed in claim 1, wherein the solvent charged with acidic gases which is obtained from the second absorption stage is regenerated in the regeneration stage in a manner such that the charged solvent is first freed from some of the dissolved acidic gases in an expansion zone by expansion of the charged solvent to a pressure below the absorption pressure, and is then freed from more of the dissolved acidic gases in a desorption zone by stripping with steam.

3. A process as claimed in claim 1 or 2, wherein the solvent in the first absorption stage contains from 0.5 to 8% by weight of water.

4. A process as claimed in claim 1 or 2, wherein the solvent in the second absorption stage contains from 1.5 to 14% by weight of water.

5. A process as claimed in claim 1 or 2, wherein the aqueous dialkyl ether phase in the extraction stage contains from 16 to 90% by weight of water.

6. A process as claimed in claim 2, wherein the water content of the regenerated solvent introduced into the first absorption stage is decreased by distilling off water beforehand.

7. A process as claimed in claim 2, wherein the solvent charged with condensable aliphatic hydrocarbons which is obtained from the first absorption stage and which is used for separating off the hydrocarbons as a hydrocarbon phase in the extraction stage is mixed with the condensed water obtained during stripping with steam in the absorption zone.

8. A process as claimed in claim 2, wherein the aqueous dialkyl ether mixture obtained in the extraction stage after phase separation is introduced into the desorption zone.

9. A process as claimed in claim 2, wherein the solvent charged with condensable aliphatic hydrocarbons is treated with water in a countercurrent extraction column in order to separate off the hydrocarbons.

* * * * *

UNITED STATES PATENT AND TRADEMARK OFFICE
CERTIFICATE OF CORRECTION

PATENT NO. : 4,414,004
DATED : November 8, 1983
INVENTOR(S) : Eckhart WAGNER et al.

It is certified that error appears in the above-identified patent and that said Letters Patent is hereby corrected as shown below:

ON FIRST PAGE PLEASE ADD:

[30]     Foreign Application Data
March 31, 1981 [DE] Fed. Rep. of Germany 3112661

Signed and Sealed this

Twenty-fourth Day of July 1984

[SEAL]

Attest:

GERALD J. MOSSINGHOFF

Attesting Officer      Commissioner of Patents and Trademarks